United States Patent [19]
Sarstedt

[11] Patent Number: 5,755,701
[45] Date of Patent: May 26, 1998

[54] BLOOD WITHDRAWAL DEVICE

[76] Inventor: Walter Sarstedt, Rommelsdorfer Strasse, 51588 Nuembrecht-Rommelsdorf, Germany

[21] Appl. No.: 377,120

[22] Filed: Jan. 23, 1995

[30] Foreign Application Priority Data

Jan. 29, 1994 [DE] Germany ............... 44 02 690.0

[51] Int. Cl.⁶ ................................... A61M 5/00
[52] U.S. Cl. ................. 604/264; 604/86; 128/763
[58] Field of Search ................. 604/264, 187, 604/200, 201, 203, 205, 86, 88, 91; 128/763–765

[56] References Cited

U.S. PATENT DOCUMENTS

| | | |
|---|---|---|
| 3,135,261 | 6/1964 | Carroll. |
| 3,366,103 | 1/1968 | Keller. |
| 4,991,601 | 2/1991 | Kasai et al.. |
| 5,286,453 | 2/1994 | Pope ........................... 604/205 |
| 5,288,466 | 2/1994 | Burns ........................ 128/763 X |

FOREIGN PATENT DOCUMENTS

| | | |
|---|---|---|
| 0026679 | 4/1981 | European Pat. Off.. |
| 0129029 | 12/1984 | European Pat. Off.. |
| 0342653 | 11/1989 | European Pat. Off.. |
| 0391461 | 10/1990 | European Pat. Off.. |
| 1462681 | 12/1965 | France. |
| 2948653 | 6/1981 | Germany. |
| 3049503 | 4/1983 | Germany. |
| 4000968 | 6/1991 | Germany. |

*Primary Examiner*—John D. Yasko
*Attorney, Agent, or Firm*—Greenblum & Bernstein P.L.C.

[57] ABSTRACT

A blood withdrawal device has a withdrawal tube 2, a stopper 14 which closes the front end of the tube, can be pierced, and is retained by a stopper cap 5 which overlaps the tube with a collar 15, and a double cannula 3 which receives the stopper cap in a guide sleeve 4. The stopper cap or the guide sleeve has at least one prominence 17 which at least indirectly deforms the stopper cap in the collar region when this is pushed into the guide sleeve, the guide sleeve is rigid and at least the prominence of the stopper cap is non-rigid, preferably flexible. By this means, on the one hand secure holding of the guide sleeve and stopper cap is possible, without a catch or screw connection, and on the other hand it is possible, in a simple, gentle manner, to couple or connect several withdrawal tubes one after another to a cannula remaining in a vein, without jerking, and to fill several withdrawal tubes with blood.

12 Claims, 4 Drawing Sheets

BLOOD WITHDRAWAL DEVICE

BACKGROUND OF THE INVENTION

The invention relates to a blood withdrawal or phlebotomy device which has a blood withdrawal tube, a stopper which closes the front end of the tube and can be pierced, and is mounted with a stopper cap which overlaps the tube with a collar, and a double cannula which can receive the stopper cap in a guide sleeve.

In a blood withdrawal device of this kind, known from German Patent DE 30 49 503 C, the cap which closes off the withdrawal tube at its front end has a cylindrical mount projecting in the axial direction. This mount has a central bore and is closed off at its front end by a pierceable closure stopper which lies on a front plate of the mount and is held by collar flanged at the front end. A tubular guide sleeve carries, in a holder at its front end, a double-ended cannula provided at both ends with a cutting edge, the end of which projecting out of the guide sleeve is used for insertion into a vein, while its rear end projects into the guide sleeve to such an extent that it pierces the closure stopper when the guide sleeve is fitted to the withdrawal tube. The guide sleeve is located in an axially movable and rotatable manner on the mount. The rear end of the cannula projecting into the guide sleeve is enveloped by a sack-like hose (valve rubber) of a length such that the cutting edge of the rear end of the cannula does not touch the base of the hose when the latter is in its normal extended state.

To connect the double cannula to the mount, the latter is provided with a holding cam projecting laterally, to which axial slits in the guide sleeve correspond. By means of the holding cam inserted into one of the axial slits, which are distributed over the circumference, rotary locking, like a bayonet closure, of the guide sleeve of the double cannula, which sits in a loose fit on the mount, can be achieved. However, such rotary locking increases the production outlay and therefore makes the blood withdrawal device correspondingly more expensive.

A withdrawal tube disclosed in European Patent EP 0 129 029 B for a blood withdrawal device is closed with a flexible stopper cap of the abovementioned type, i.e. the cap is pushed with a stopper into the open end of the tube and has a collar which overlaps the tube, preferably with clearance. The stopper cap, covering the withdrawal tube like a collar, prevents blood from splashing when the filled withdrawal tube is pulled off. To prevent an aerosol effect, it is necessary for the stopper to be pulled off together with the stopper cap. This means that the stopper cap must be made of a material which prevents deformation of the contact surface. The flexibility of the stopper cap is limited by the holding function with the stopper. The guide sleeve of this withdrawal tube, when used in practice, is of a considerably larger diameter than the stopper cap, and a certain dexterity is required of a person taking blood from a patient, in order to be able to perform a proper blood withdrawal which is gentle on the patient in spite of the wide clearance of the guide. However, since no particular catch or holding connections are provided, this blood withdrawal device can be produced with a correspondingly reduced outlay.

Finally, German Patent DE 29 48 653 C discloses a blood withdrawal device which likewise has a closure cap with a mount projecting in the axial direction. The guide sleeve of the double cannula can be pushed onto an adaptor piece of the mount of the closure cap, which is screwed onto an external thread of the blood withdrawal tube. Both the closure cap with the mount and adaptor piece, and the guide sleeve, are made of thermoplastic. The adaptor piece has, behind the closure stopper, a pipe socket with a conical bore, which, to hold the double cannula, is mounted on the correspondingly conical mount, which forms one piece with the closure cap. It has been found with this type of connection that it is either too tight or undesirably loose; too tight a fit can lead to the cannula being pushed through the vein of the patient when the withdrawal tube is attached, because of the associated jerky transition. Another disadvantage of this type of withdrawal device arises if the guide sleeve is deform able. In particular, when the blood withdrawal tube is connected to the guide sleeve after introduction of the cannula into the vein of the patient, in addition to the penetration resistance of the needle and stopper, which is applied by the thumb and index finger, for example, on the fixing sleeve containing the cannula, the radial force of the non-circular guide sleeve also must be overcome. Since a uniform force cannot be applied, coupling without jerking is not possible.

The invention has the object of providing a blood withdrawal device of the abovementioned general type which allows, without catch or screw connections, on the one hand secure holding of the guide sleeve and stopper cap, and thereby on the other hand allows, in a simple and gentle manner, several withdrawal tubes to be coupled or connected without jerking to a cannula remaining in the vein, and for several withdrawal tubes to be filled with blood.

SUMMARY OF THE INVENTION

This object is achieved according to the invention by a device in which the stopper cap or the guide sleeve is constructed with at least one prominence which at least indirectly deforms the stopper cap in the collar region when this is pushed into the guide sleeve, and the guide sleeve is constructed rigidly and at least the prominence of the stopper cap is constructed non-rigidly, preferably flexibly. A self-clamping location of the guide sleeve directly on the collar of the stopper cap can thus be achieved in an astonishingly simple manner. It has been recognized and correspondingly utilized that, by interaction of the rigid guide sleeve, which is preferably made of thermosetting plastic and if necessary is also additionally reinforced by stiffening ribs on its outer surface, and the flexible stopper cap and/or non-rigid prominence or projection when the guide sleeve and stopper cap are joined or pushed into one another, a flow of forces which causes the self-clamping connection or holding can be achieved on the basis of at least one prominence, and regardless of whether this is located on the inner surface of the rigid guide sleeve or on the outer surface of the collar of the stopper cap. In fact, the deformation of the flexible stopper cap and/or of the prominence can be utilized for a rigid connection of the double cannula and withdrawal tube, whereby even relatively large tolerances can be bridged.

This effect can be promoted if, between the collar of the stopper cap and the withdrawal tube, there is a clearance, which also helps to prevent the aerosol effect. However, it is possible to design the stopper cap such that the collar lies against the blood withdrawal tube. In order to allow deformation which effects holding, the prominence, or the prominences, would then in all cases have to be designed flexibly or non-rigidly, for example by a corresponding choice of material and/or by hollow spaces or recesses provided in the prominence which allow or contribute to the non-rigid character. The prominence can be constructed, for example, in the form of a conical thickening or circumferential bulge, a punctiform accumulation of material or a longitudinal rib which merges into a wedge surface in its end section. If several prominences are provided, these should be located in distribution over the circumference of the stopper cap or of the collar.

The prominence or prominences can be so designed that when the guide sleeve and stopper cap are pushed into one another, the prominence comes into contact with the guide sleeve or stopper cap only after a certain travel, in particular when the rear end of the double cannula just penetrates into or through the valve rubber. As soon as the penetration force is removed, the flexible stopper cap and/or the prominence is/are deformed and the rigid, self-clamping holding is thus achieved. The prominence can be designed here such that when the components are pushed into one another, the force or counter-pressure builds up slowly, i.e. is increased gradually, and is decreased correspondingly gradually and slowly when the components are pulled apart, i.e. if several samples must be taken. There are no jerky transitions, so that penetration of the cannula through the vein of the patient is prevented.

BRIEF DESCRIPTION OF THE DRAWINGS

Further features and advantages of the invention can be seen from the appended claims and the following description, in which examples of blood-withdrawal devices embodying the invention, shown in diagram form in the drawings, are explained in more detail. In the drawings:

DESCRIPTION OF PREFERRED EMBODIMENTS

Figure 3:
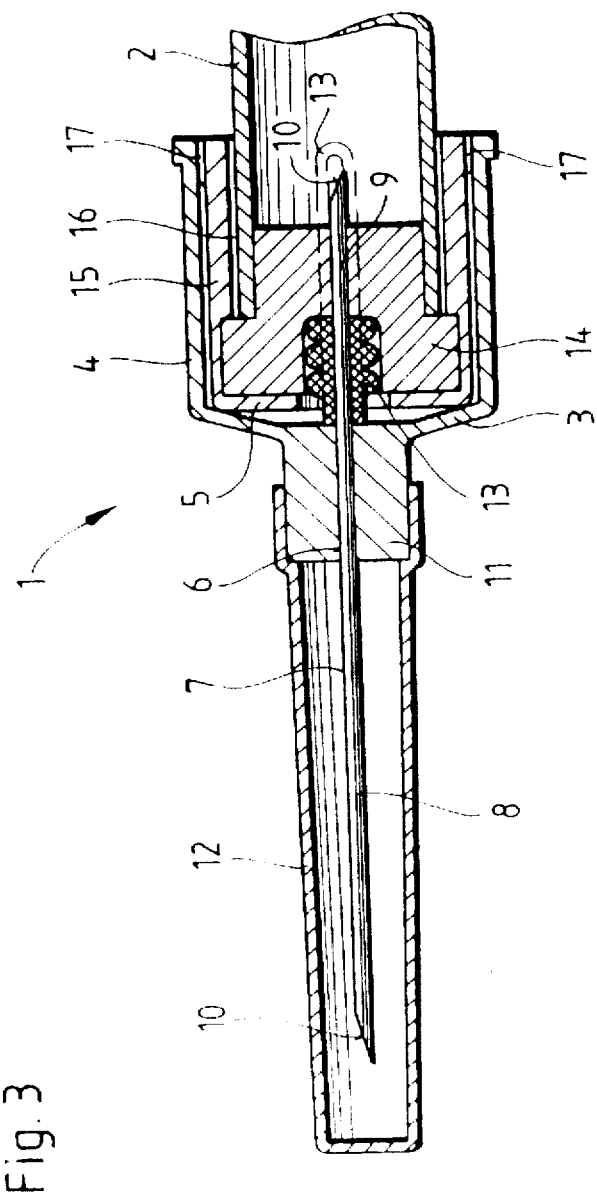
FIG. 3 shows a longitudinal section of a blood withdrawal device in which the withdrawal tube show n in FIG. 1 is located in a self-clamping manner by means of the stopper cap in a guide sleeve of a double cannula mounted on the stopper cap.

FIG. 3 shows a blood withdrawal device 1 which comprises a withdrawal tube 2 and a double cannula 3 which is pushed, with an integral guide sleeve 4, onto a stopper cap 5 which closes the front end of the withdrawal tube 2. The guide sleeve 4 is made of a rigid, thermosetting plastic material. The double cannula 3 is fitted with a needle or cannula holder 6 which accommodates the cannula 7, the front and rear cannula end 8 and 9 of which are sharp, i.e. provided with cutting edges 10. The front cannula end 8 is used for insertion into a vein; as long as the double cannula 3 or the blood withdrawal device 1 is not in use, it is protected by a removable sleeve or cover 12 located on a cylindrical mounting boss 11 of the guide sleeve 4. The rear cannula end 9 projects beyond the cannula holder 6 into the guide sleeve 4; it is enclosed by a hose-like valve rubber 13 of length such that when the cannula 3 is, initially, separate from the tube 2, the cutting edge 10 of the rear cannula end 9 does not touch the base of the valve rubber 13 when this is in its normal extended state. The withdrawal tube 2 can be of a type such that it operates either by the suction piston principle or by the vacuum principle.

Figure 2:
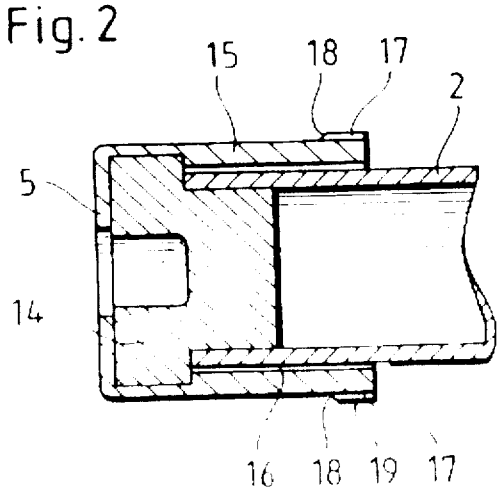
FIG. 2 shows the subject tube and stopper cap according to FIG. 1 in cross-section.

The stopper cap 5, made of a flexible plastics material, is held on the tube by a stopper 14 of rubber which engages in the withdrawal tube 2. It has, as shown in FIG. 2, a collar 15, which overlaps the outer wall of the withdrawal tube 2 with a small clearance 16. On the outside or outer jacket of the stopper cap 5 are located several prominences or projections 17 distributed over the circumference, which are constructed rib-like, in the form of wedge-shaped bevels 18 at the forward ends, which then merge into a straight section 19.

For blood withdrawal, the double cannula 3 and the withdrawal tube 2 are pushed into one another, i.e. the rigid guide sleeve 4 is pushed onto the flexible stopper cap 5, as shown in FIG. 3. During this operation, the base of the valve rubber 13 first meets the rubber stopper 14, the valve rubber 13 being pushed together like a concertina, as indicated in FIG. 3; during further insertion and the cutting edge 10 of the rear cannula end 9 comes into contact with the base of the valve rubber 13. Pushing the components further into one another causes the cutting edge 10 of the rear cannula end 9 to pierce first the valve rubber 13 and then the rubber stopper 14.

The prominences 17, which increase the circumference of the flexible stopper cap 5 from a certain region, are located and designed to make an interference fit with the sleeve 4, such that at this moment, i.e. as soon as the penetration force disappears, the prominences 17 come gradually and increasingly more into contact with the guide sleeve 4 via their rising wedge-shaped bevels 18, whereupon a deformation of the stopper cap 5, assisted by the clearance 16 between the stopper cap 5 and the withdrawal tube 2, is established. This causes a self-clamping connection of the double cannula 3 and withdrawal tube 2, in particular via the guide sleeve 4 pushed onto the stopper cap 5. The wedge-shaped bevels 18 promote a slow build-up of force with a correspondingly gradually increasing counter-pressure when the components are pushed into one another, and a correspondingly gentle decrease in force when the components are pulled apart, whereby jerky transitions can be avoided. This facilitates withdrawal, in a manner which is gentle on the patient, of several blood samples with the same double cannula, the front cannula end 8 of which remains in the vein of the patient while the withdrawal tube 2 is changed.

Figure 1:
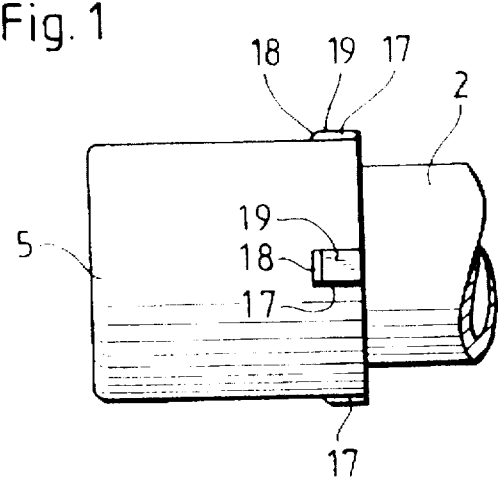
FIG. 1 shows as a detail a side view of the front end, closed by a stopper cap, of a withdrawal tube of a blood withdrawal device according to a first embodiment of the invention.
Figure 4:
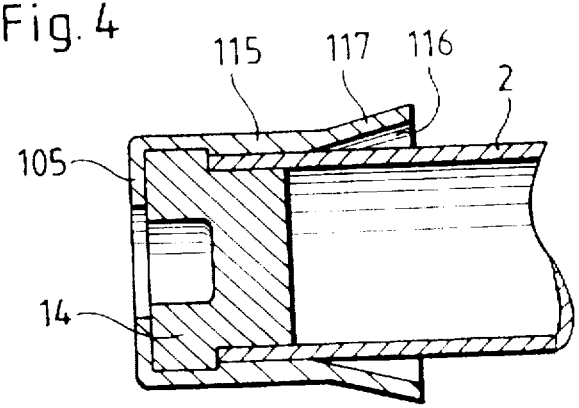
FIG. 4 s hows a cross-section of the front end of a withdrawal tube closed by another construction of a stopper cap.

FIG. 4 shows a stopper cap 105, which differs from that shown in FIGS. 1 to 3 only in respect of the shape of the prominence 117. This cap has a collar 115 which initially lies on the front end of the withdrawal tube 2 without clearance, before it then merges into an end cone which widens towards the end, forms the prominence 117 and overlaps the withdrawal tube with an increasingly larger clearance 116. As soon as the guide sleeve 4 (optionally provided with prominences on its internal wall) enters the region of the conical prominence 117 when the guide sleeve 4 (cf. FIG. 3) and withdrawal tube 2 are pushed into one another, deformation of the flexible stopper cap 105 is also established in this case, in particular in the region of the conical prominence 117. A slow build-up of force, already described above, when the components are pushed into one another, and a correspondingly gentle decrease in force when the components are pulled apart, is achieved, i.e. without causing jerky transitions.

Figure 5:
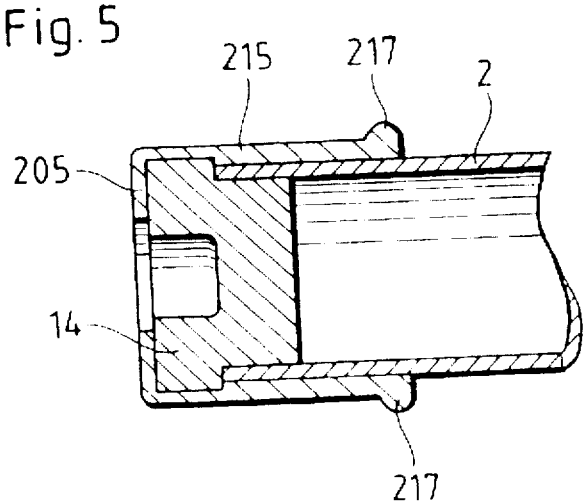
FIG. 5 shows a cross-section of the front end of a withdrawal tube close d by a still further construction of a stopper cap.
Figure 6:
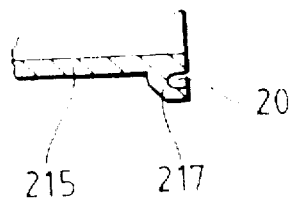
FIG. 6 shows a detail of FIG. 5, on a larger scale, of the rear region, constructed with a prominence, of the stopper cap shown folded away downwards in the plane of the drawing.

Another embodiment of a stopper cap 205, which is also based on the principle described above for pushing the components into one another and pulling them apart without jerking, is shown in FIG. 5. The collar 215 of this stopper cap lies against the outer jacket of the withdrawal tube 2 without clearance. The flexibility which ensures the deformation and therefore the self-clamping holding of the guide sleeve 4 of the double cannula 3 on the stopper cap 205 is displaced here to the region of the prominence 217 constructed as a cam or circumferential bulge of flexible material in this embodiment. To contribute the flexibility or non-rigid character of the prominence 217 (cam, circumferential bulge etc.), it can be made additionally flexible—as shown in diagram form in FIG. 6—by a hollow space 20. The self-clamping holding of the guide sleeve 4 on the stopper cap 205 is thus achieved as soon as the guide sleeve 4 is pushed over the prominence 217.

Figure 7:
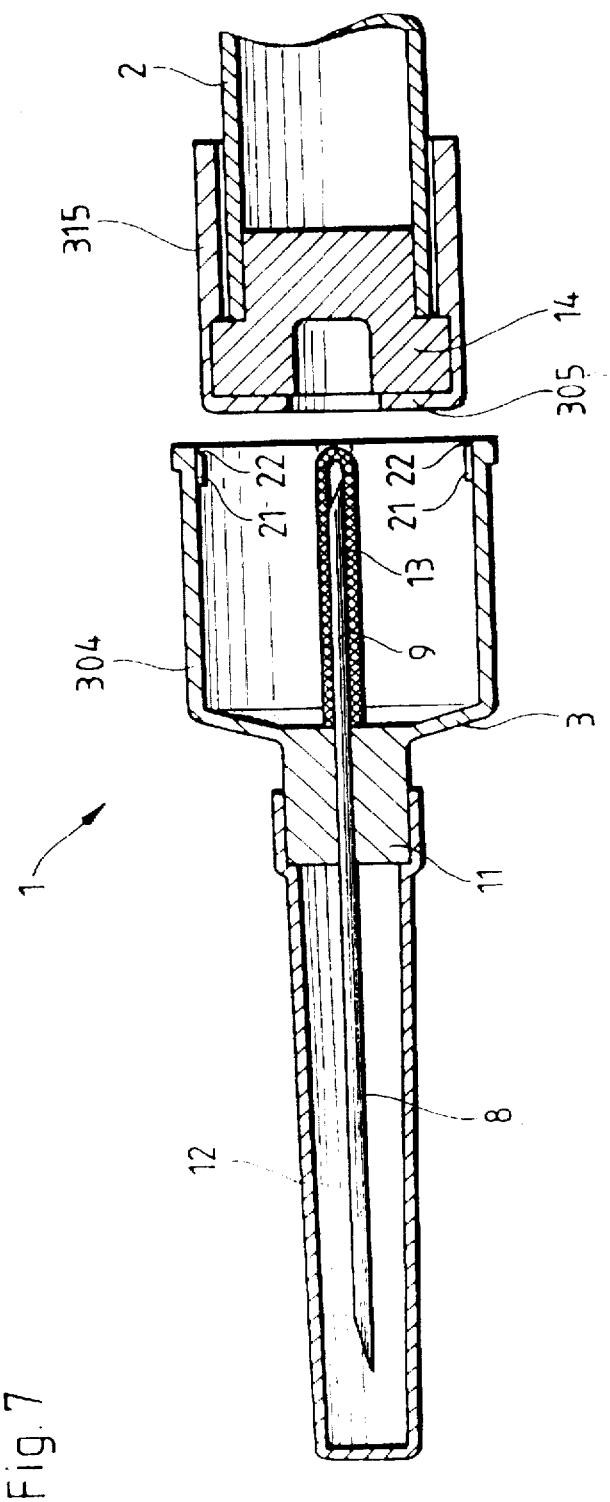
FIG. 7 shows a longitudinal section of an embodiment of a blood withdrawal device in which non-rigid, flexible prominences are arranged on the inner jacket of the guide sleeve and provide a self-clamping connection when the guide sleeve is pushed onto the stopper cap, shown as an exploded view.

In the blood withdrawal device 1 shown in FIG. 7, the self-clamping mounting of the rigid guide sleeve 304 of the double cannula 12 on the stopper cap 315 is achieved by non-rigid, flexible prominences 21 arranged on the inner surface of the guide sleeve 304. The said prominences 21 are provided, on their ends facing the stopper cap 315, with wedge-shaped bevels 22 which, in this case too, promote a gradually increasing, slow build-up of force, thereby achieving a jerk-free transition when the stopper cap 315 with the withdrawal tube 2 is pushed into the guide sleeve 304; a correspondingly gentle decrease in force is achieved when the withdrawal tube 2 with the stopper cap 315, is removed from the guide sleeve.

In this embodiment the collar 315 is spaced from the wall of the tube 2 and is deformable by the prominences 21. In a further modification the prominences 21 may be rigid, and the grip between them and the collar is provided by the collar when it is deformed by the prominences.

I claim:

1. A blood withdrawal device comprising:
   a withdrawal tube for receiving blood, said tube having an open end;
   a stopper for closing said open end of said tube;
   a stopper cap for fitting over said stopper and said open end and for retaining said stopper in said open end of said tube, said stopper cap further comprising a collar overlapping an outer wall of said withdrawal tube extending from said open end toward a closed end of said tube; and
   a double cannula comprising a guide sleeve, with a respective cannula end on each opposite side of said guide sleeve, said guide sleeve being adapted to fit removably over an exterior of said stopper cap for attaching said cannula to said withdrawal tube, such that when so attached, one said end of said double cannula pierces said stopper providing communication between the other end of said cannula and an interior of said withdrawal tube;
   wherein said guide sleeve is substantially rigid, and at least one of said stopper cap and said guide sleeve incorporates at least one radial prominence arranged to make an interference fit with the other of said stopper cap and said guide sleeve such that at least one of said collar and said prominence is deformed when said guide sleeve is fitted over said collar, whereby said guide sleeve and said collar are in mutually gripping relation for holding said withdrawal tube and double cannula separably together.

2. The blood withdrawal device claimed in claim 1 in which said at least one prominence is provided internally on said guide sleeve.

3. The device claimed in claim 1 in which said prominence is provided externally on said collar.

4. The device of claim 1 in which the prominence is deformable.

5. The device of claim 1 in which the collar is deformable.

6. The device of claim 1 in which said prominence is spaced axially from the end of said stopper cap or guide sleeve.

7. The device of claim 1 in which the collar is spaced radially from the withdrawal tube over at least part of the length of the collar.

8. The device of claim 1 in which said prominence is adapted to provide a progressively increasing interference fit between said guide sleeve and collar as these are brought into mutual engagement.

9. A blood withdrawal device comprising:
   a withdrawal tube;
   a stopper which closes a front end of said tube and can be pierced;
   a stopper cap which retains said stopper in closing relationship with said front end of said tube, said stopper cap further comprising a collar which overlaps an outer wall of said tube; and
   a double cannula which is provided with a guide sleeve, which removably receives said stopper cap;
   wherein said stopper cap or said guide sleeve has at least one prominence which at least indirectly deforms said collar when said collar and stopper cap are pushed into said guide sleeve, said guide sleeve being rigid, and at least said prominence of said stopper cap or of said guide sleeve being non-rigid.

10. The device of claim 1, wherein, during insertion of said stopper cap, stopper and tube into said guide sleeve, said end of said double cannula pierces said stopper prior to interference of said at least one radial prominence with said other of said stopper cap and said guide sleeve.

11. The device of claim 9, wherein, during insertion of said stopper cap, stopper and tube into said guide sleeve, said stopper is pierced before said at least one prominence at least indirectly deforms said collar.

12. A blood withdrawal device comprising:
   a withdrawal tube for receiving blood, said tube having an open end;
   a stopper for closing said open end of said tube;
   a stopper cap for fitting over said stopper and said open end and for retaining said stopper in said open end of said tube, said stopper cap further comprising a collar overlapping an outer wall of said withdrawal tube extending from said open end toward a closed end of said tube; and
   a double cannula comprising a guide sleeve, with a respective cannula end on each opposite side of said guide sleeve, said guide sleeve being adapted to fit removably over an exterior of said stopper cap for attaching said cannula to said withdrawal tube, such that when so attached, one said end of said double cannula pierces said stopper providing communication between the other end of said cannula and an interior of said withdrawal tube;

wherein said guide sleeve is substantially rigid, and at least one of said stopper cap and said guide sleeve incorporates at least one radial prominence arranged to make an interference fit with the other of said stopper cap and said guide sleeve such that at least one of said collar and said at least one prominence is deformed when said guide sleeve is fitted over said collar, whereby said guide sleeve and said collar are in mutually gripping relation for holding said withdrawal tube and double cannula separably together; and wherein said at least one prominence is formed such that, during insertion of said stopper cap, stopper and tube into said guide sleeve, said at least one prominence is finally deformed when a penetration force of said end of said double cannula piercing said stopper ceases on account of said end of said double cannula penetrating said stopper.

\* \* \* \* \*